United States Patent [19]

Bodicky

[11] Patent Number: 4,613,329
[45] Date of Patent: Sep. 23, 1986

[54] CATHETER PLACEMENT DEVICE

[75] Inventor: Raymond O. Bodicky, Oakville, Mo.

[73] Assignee: Sherwood Medical Company, St. Louis, Mo.

[21] Appl. No.: 537,913

[22] Filed: Sep. 30, 1983

[51] Int. Cl.⁴ ............................................. A61M 5/00
[52] U.S. Cl. .................................. 604/158; 604/163; 604/243; 604/165
[58] Field of Search .............................. 604/158-169, 604/171, 172, 240-243, 283

[56] References Cited

U.S. PATENT DOCUMENTS

| | | | |
|---|---|---|---|
| 2,820,457 | 1/1958 | Phillips | 128/351 |
| 3,185,151 | 6/1962 | Czorny | 604/163 |
| 3,305,616 | 5/1962 | Hamilton | 604/243 |
| 3,633,579 | 1/1972 | Alley | 128/214.4 |
| 3,682,173 | 8/1972 | Center | 128/214.4 |
| 3,703,174 | 11/1972 | Smith | 128/214.4 |
| 3,730,187 | 5/1973 | Reynolds | 128/349 R |
| 3,765,420 | 10/1973 | Felczak | 128/347 |
| 3,825,001 | 6/1974 | Bennet et al. | 604/163 |
| 3,826,256 | 7/1974 | Smith | 128/214.4 |
| 3,903,885 | 10/1975 | Fuchs | 604/158 |
| 4,076,285 | 2/1978 | Martinez | 604/242 |
| 4,149,535 | 4/1979 | Volder | 128/214.4 |
| 4,187,848 | 2/1980 | Taylor | 128/247 |
| 4,287,891 | 9/1981 | Peters | 128/347 |
| 4,327,723 | 5/1982 | Frankhauser | 604/171 |
| 4,345,606 | 8/1982 | Littleford | 128/784 |
| 4,419,094 | 12/1983 | Patel | 604/165 |

FOREIGN PATENT DOCUMENTS 3147609 6/1983 Fed. Rep. of Germany.

Primary Examiner—C. Fred Rosenbaum
Assistant Examiner—Karen L. Kaechele
Attorney, Agent, or Firm—Stanley N. Garber; Andrew J. Beck; William R. O'Meara

[57] ABSTRACT

A catheter placement device is provided which includes an adapter with an elastomeric grommet having a bore through which a pliable catheter is fed into a blood vessel of a patient. The grommet has a flange engageable with the catheter and effects a relatively low resistance to distal movement of the catheter and relatively high resistance to proximal movement of the catheter. A pair of adapters may be used with one adapter carrying a grommet and the other having a frusto-conical bore receiving an end of the grommet. The adapters are relatively rotatable to cause the grommet to lock the catheter against axial movement relative to the adapters. Retention members may be used to prevent inadvertent separation of the adapters during relative rotation.

21 Claims, 12 Drawing Figures

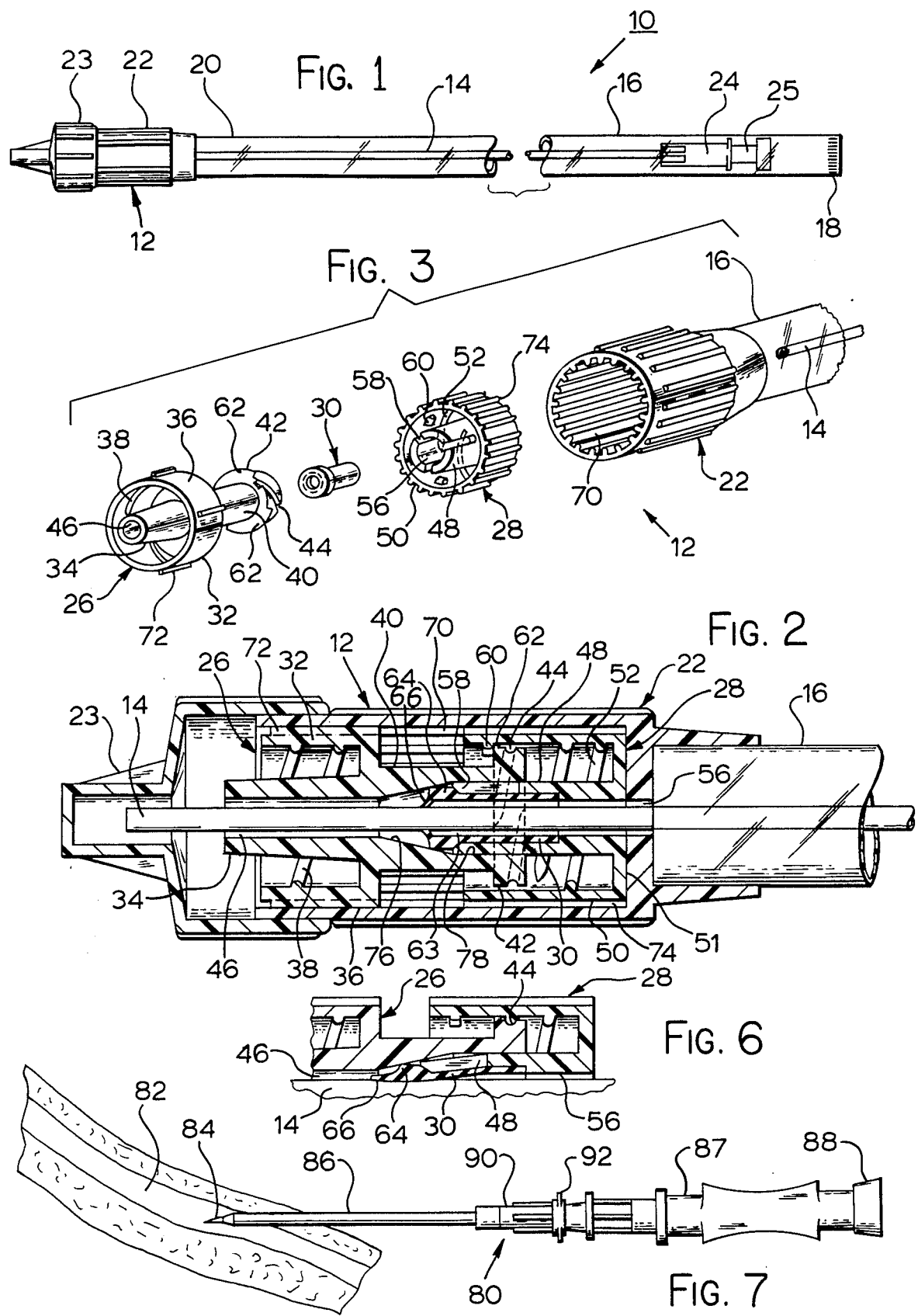

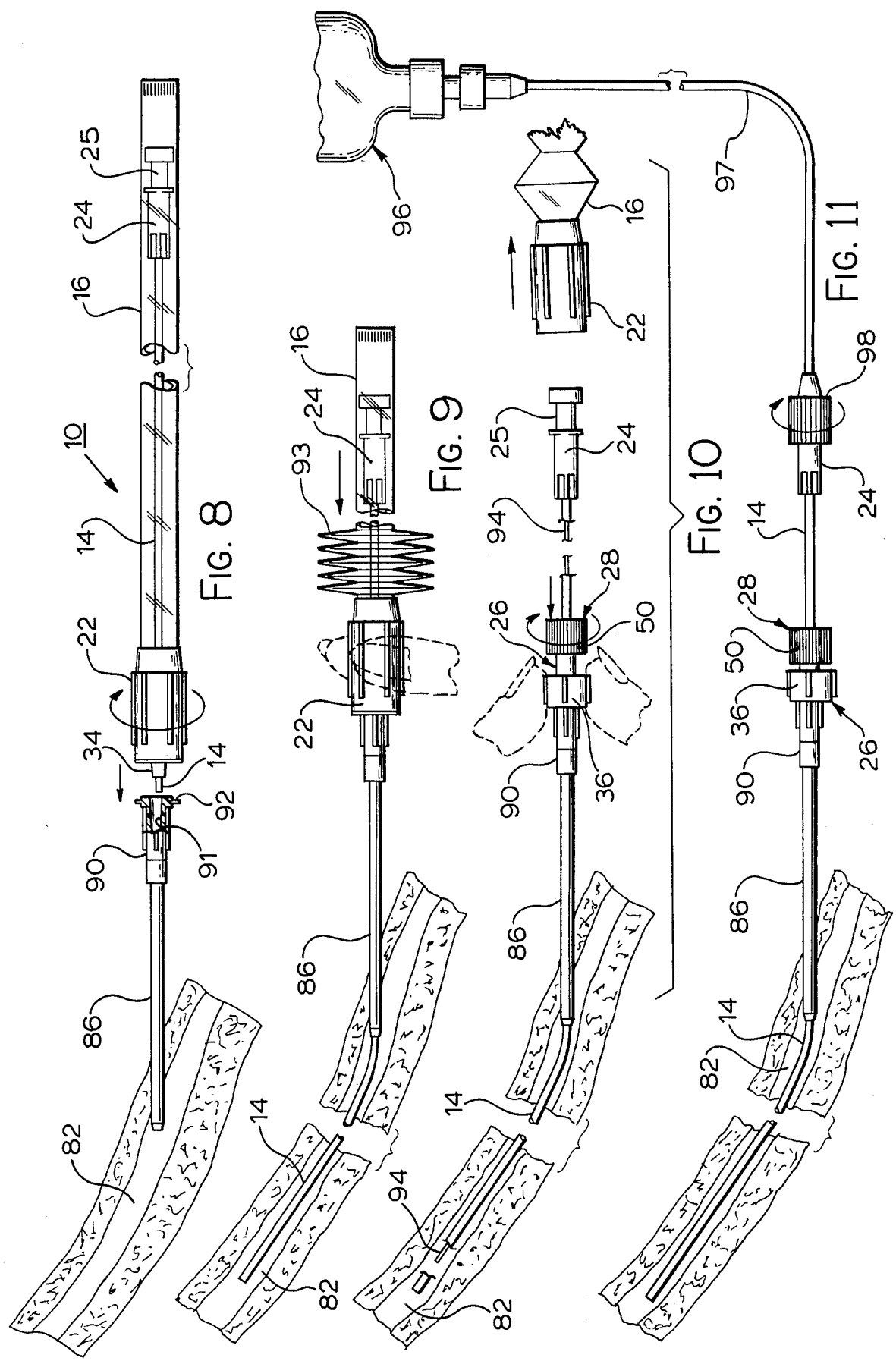

CATHETER PLACEMENT DEVICE

DESCRIPTION

1. Technical Field

This invention relates to catheter placement devices and more particularly to a catheter placement device having a catheter that is fed into a patient through an introducer catheter.

2. Background Art

Relatively small pliable or flexible catheters are often inserted into a patient, such as into a venous or arterial blood vessel, for various purposes. For example, it may be disirable to introduce a substance at a point in the blood system that is not readily accessible except by feeding a catheter along a body vessel. Such catheters may be used in diagnostic procedures where a long catheter is threaded through a vein or an artery into the chambers of the heart for the introduction of X-ray contrast dye in order to observe blood flow patterns. Also, such catheters may be employed to obtain deep body blood pressure measurements or to introduce a drug or an infusion liquid at a preselected point in the venous system. There are, of course, other reasons for feeding a catheter into a blood vessel of a patient in order to place the end of the catheter a substantial distance from the point of entrance into the vessel.

Such catheters are generally inserted into a patient, by first employing a catheter introducer cannula and needle. For example, with the introducer needle extending beyond the distal end of the introducer cannula, the two are moved through the skin and into the blood vessel. The needle is removed while the cannula remains in the blood vessel. The end of the pliable catheter is then moved through the introducer cannula and into the blood vessel to a desired location, which in some cases, may be at a considerable distance from the introducer catheter.

There have been certain problems or disadvantages associated with prior art devices of this type. Generally, the catheter, which is usually disposed in a flexible protective sleeve to maintain its sterility, is threaded or fed into the patient in incremental steps. That is, the sleeve and catheter are usually grasped at a given location and then moved distally to move the catheter an incremental distance into the vessel. This movement causes the sleeve to collapse axially or become folded in accordian-like fashion. The catheter and sleeve are released and then again grasped at a different location, and again moved distally to again move the catheter a further distance into the blood vessel. In some cases, when the catheter and sleeve are released in order to grasp them at a new location, the catheter moves proximally or tends to return to its previous location. This undesired return movement of the catheter may be due to the catheter reaching a curve in the blood vessel or to the axially folded portion of the sleeve, when released, tending to straighten and effect return or proximal movement of the catheter. Such return movement makes the procedure more difficult and increases the time and number of incremental insertion steps necessary to locate the catheter at the desired location within the vessel.

Another problem with some prior devices is that it is difficult to accurately hold the catheter in place once it is in a selected location, especially where the catheter has a small diameter. Special care must be taken to hold the catheter in place while securing it to the patient and when connecting the catheter to other apparatus such as a source of dye, infusion liquid, or other device. While some catheter devices employ a form of locking to secure the catheter relative to the introducer cannula through which it is fed, such devices have not been entirely satisfactory. For example, in one device, a catheter is fed through a cylindrical rubber-like grommet with its opposite end walls engaged respectively with a pair of threadedly coupled members. When the members are moved sufficiently toward each other, the grommet bulges into tight frictional engagement with the catheter to lock it or hold it stationary relative to the members. Generally, a relatively large effort is required to lock the catheter. Also, such members may inadvertently separate if one member is inadvertently rotated too far when unlocking the catheter. With some devices, the catheter locking mechanism is not highly reliable so that the catheter locking effect may fail.

SUMMARY OF THE INVENTION

It is therefore an object of the present invention to provide an improved catheter placement device which overcomes one or more of the above-mentioned problems.

A more specific object is to provide a catheter placement device wherein feeding of the catheter into the patient is especially easy and can be readily accurately performed.

A still further object is to provide a catheter placement device of the above type which is simple to operate and which provides improved locking means for the catheter.

Still another object of the present invention is to provide an improved catheter placement device of the above type which has a pair of relatively rotatable members for locking and unlocking a catheter wherein such members are prevented from separating due to inadvertent excessive rotation.

In accordance with one aspect of the present invention, a catheter placement device is provided which includes an adapter, a resiliently compressible grommet in the adapter having a bore with a restriction, and an elongate flexible catheter slidable in the bore for insertion into the patient and which is engagable with the restriction. The restriction effects a greater resistance to movement of the catheter in the proximal direction than in the distal direction.

In accordance with another aspect of the present invention a catheter placement device is provided which includes a luer adapter having one end adapted for connection with an introducer catheter that is adapted for insertion into a patient. The device includes a catheter locking adapter threadedly connected to the other end of the luer adapter, and a resiliently compressible grommet. A pliable catheter is movable through the bores in the adapters and grommet and is adapted for insertion into the patient. The bore of one of the adapters is tapered and receives a portion of the grommet. Relative rotation of the adapters effects increased frictional engagement between the grommet and catheter to hold the catheter stationary with respect to one of the adapters.

In accordance with still another aspect of the invention, a catheter placement device is provided which has a pair of threadedly coupled adapters having a grommet between them for locking a catheter extending through the grommet. The adapters have complementary abutment members allowing relative rotation but preventing inadvertent separation of the members.

These, as well as other objects and advantages of the present invention, will become apparent from the following detailed description and accompanying drawings.

BRIEF DESCRIPTION OF THE DRAWINGS

FIG. 1 is an elevational view of a catheter placement device in accordance with a preferred embodiment of the present invention;

FIG. 2 is an enlarged longitudinal cross sectional view of the left end portion of the device of FIG. 1 with the catheter in an unlocked condition;

FIG. 3 is an exploded perspective view, on an enlarged scale, of parts of the device of FIG. 1;

FIG. 6 is a fragmentary cross-sectional view similar to FIG. 2 but showing only some parts and illustrating the relationship of certain parts of the device when the catheter is in a locked condition;

FIG. 7 is an elevational view of an introducer catheter and needle assembly shown introduced into a body vessel;

FIG. 8 is an elevational view of the device of FIG. 1 illustrating a step in connecting the device to the introducer catheter of FIG. 7 after the introducer needle has been removed;

FIG. 9 illustrates a step of advancing the catheter of the device of FIG. 1 through the introducer catheter of FIG. 8 and into a body vessel;

FIG. 10 illustrates a step in locking the catheter relative to parts of the device of FIG. 1;

FIG. 11 is an elevational view illustrating the step of connecting an infusion supply source to the catheter after the catheter is disposed in the body vessel in a desired location.

DETAILED DESCRIPTION OF PREFERRED EMBODIMENTS

Figure 4:
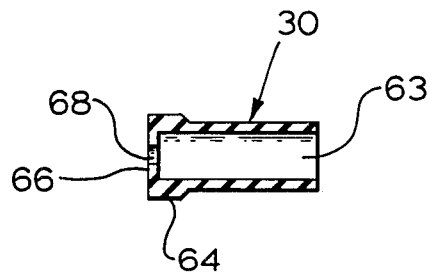
FIG. 4 is a longitudinal cross-sectional view of the grommet shown in FIG. 3 on an enlarged scale.

Referring now to the drawings and more particularly to FIGS. 1-3, a catheter placement device 10 is shown including a catheter locking assembly indicated generally at 12, a flexible or pliable catheter 14 extending into the assembly 12, and a collapsible protective sleeve 16 surrounding the catheter 14. Sleeve 16 is generally tubular and may be closed, if desired, at its proximal end 18 such as by a heat seal or cement, and is sealingly connected at its distal end 20 to the distal end portion of a generally cylindrical sleeve adapter or connector 22 of assembly 12 such as by a suitable cement, bonding operation or mechanical joint. A removable, protective end closure cap 23 is connected to the distal end of adapter 20 to close the distal end of the device 10 including catheter 14. Cap 23 may be of a suitable plastic and secured in place by means of a friction fit with the distal end of adapter 22. The collapsible sleeve 16 is preferably made of a thin flexible transparent material, for example, a suitable plastic such as a polyethylene film.

The catheter 14 may be formed of a soft pliable or flexible plastic such as urethane, silicone rubber, polyvinyl chloride or other soft thermoplastic material which will not cause damage to the patient. Catheter 14 is shown including a conventional female luer lock connector or hub 24 at the proximal end. A stylet 25 is shown disposed in the catheter, and may be used to stiffen the catheter to assist feeding the catheter into a patient. Where catheter 14 is very pliable or supple and is of small diameter, the stylet is especially beneficial during catheter insertion.

As seen in FIGS. 2 and 3, the catheter locking assembly 12 includes a luer adapter or connector 26, a catheter locking adapter or connector 28, and a resiliently compressible grommet 30, all shown in sleeve connector 22 in FIG. 2. These members cooperate to lock and unlock catheter 14 which extends through them, as will be discussed in detail hereafter.

Luer adapter 26 includes a conventional male luer lock connector 32 at the distal end which has a luer tapered, slip connector 34 surrounded by a luer lock collar 36 having internal luer lock threads 38. Connector 32 is adapted to be connected to a complementary female luer lock connector or hub of an introducer catheter as will be described herein. The adapter 26 has a proximally extending portion 40 having a flange 42 at the distal end that is provided with peripheral threads 44. A passage or bore 46 extends through the luer adapter 26 and is adapted to receive the catheter 14. Adapter 26 may be made of a relatively hard or rigid plastic such as polycarbonate, polypropylene or other suitable plastic.

The catheter locking adapter 28 includes a central distally extending portion or collet 48 and a collar 50 surrounding in spaced relation and integrally connected with the collet 48 by an integral proximal end wall 51 (FIG. 2). Collar 50 is provided with internal threads 52 that are adapted to be threadedly connected with threads 44 on luer adapter 26. The catheter locking adapter 28 has a passage or bore 56 extending through it and which receives the grommet 30. The collet 48 has a plurality of circumferentially spaced longitudinally or axially extending slots 58 which increase the resiliency of the collet. Collet 48 is shown having three slots. Adapter 28 may be made of a suitable plastic such as a relatively rigid polypropylene or the like but which provides a relatively flexible collet 48. Also disposed on the inner sidewall of collet 48 and spaced from the threads 52 are a plurality of equally circumferentially spaced detents or radial abutments 60. Two of the detents 60 are in view in FIG. 3. These detents could be replaced by a ring if desired. These detents cooperate with a pair of radial flanges or snap ears 62 on flange 42 of luer adapter 26. When the adapters 26 and 28 are assembled the ears 62 snap over the detents 60 placing the threads 44 of adapter 26 in condition for threaded engagement with the threads 52 on collar 50 and with the detents thereafter preventing inadvertent separation of the adapters when one is rotated relative to the other when the device is in use. The parts are shown assembled in FIG. 2 and with the device 12 in the unlocked condition, that is, with the catheter 14 capable of being manually moved in either direction through the adapters 26 and 28 and grommet 30.

The grommet 30 is formed, such as by molding, of a resiliently compressible or elastomeric material such as rubber or soft plastic, for example, a plastic of synthetic rubber or plastic commercially known as Kraton may be used. The grommet, which is shown in its free state in FIGS. 3 and 4, is generally cylindrical and has a bore or passage 63 extending through it for receiving the catheter 14. The grommet has an enlarged head 64 at the distal end which has a greater outer diameter than the outer diameter of the rest of the body of the grommet and a greater cross-sectional wall thickness than the rest of the body. At the distal end of head 64 is a radially inwardly extending annular flange 66 partially closing or restricting the distal end of bore 63 and completely surrounding the catheter 14. The flange has an opening 68 which is normally, or in the free state of the grommet, of somewhat smaller diameter than that of bore 63 and the outer diameter of catheter 14 so that, when the catheter 14 is inserted through the bores of adapters 26 and 28 and the bore 63 of the grommet 30, the flange 66 bends slightly in a distal direction away from the distal end of the grommet and bore 63 and lies against the outer surface of the catheter 14 as shown for illustration in FIG. 2. In the unlocked condition of device 12 (FIG. 2), the annular flange 66 is in frictional engagement with catheter 14 but effects only a slight resistance to movement of the catheter 14 in the distal direction so that it can be easily and accurately moved to a desired location in the patient in use of the device 10.

Figure 5:
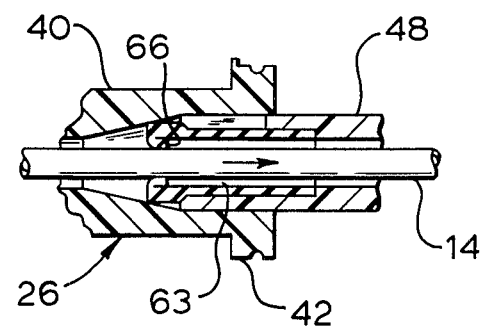
FIG. 5 is a fragmentary cross-sectional view similar to FIG. 2 but showing only some parts of the device and illustrating the condition of the device when the catheter is moved through the grommet in a proximal direction.

When the catheter 14 is moved in a proximal direction either manually or by other forces, as will be further discussed, the annular flange 66 is bent or turned inwardly into bore 63 by the catheter 14 and is wedged and compressed into the space between the inner walls of the bore 63 and the outer walls of the catheter, as illustrated in FIG. 5. With the annular flange 66 turned into bore 63, the flange 66 effects a resistance to proximal movement of the catheter (direction of the arrow in FIG. 5) relative to the grommet 30 which is substantially greater than the resistance the grommet effects to movement of the catheter in the distal direction relative to the grommet. The radial dimension, as seen in FIG. 4, of flange 66 between the bore 63 and opening 68, and the axial width or thickness of the flange may be made greater than the average radial distance between the outer surface of catheter 14 and the inner surface of bore 63 of the grommet 30 as seen in FIG. 5 so as to effect a substantial amount of friction between the catheter and the grommet and effect a relatively high resistance to movement of the catheter in the proximal direction. As will be further discussed herein, the relatively high resistance to catheter movement in the proximal direction prevents undesirable return movement of the catheter during insertion into a patient.

As best seen in FIGS. 2 and 3, the radially inner wall of sleeve adapter or connector 22 is provided with longitudinally extending, circumferentially spaced splines 70 which receive and cooperate with longitudinally extending, circumferentially spaced, splines 72 and 74 on the outer walls of adapter collars 36 and 50, respectively. The adapter members 26 and 28 are shown in axially aligned operative relation within the sleeve connector 22 in FIG. 2. The splines 70 on connector 22 enter the spaces between and engage the splines 72 and 74 to maintain the adapters 26 and 28 in fixed rotational relationship but this splined connection allows the sleeve connector 22 to slide axially relative to each of the adapters 26 and 28 and to be removed from the adapters if desired. Rotation of sleeve connector 22 will rotate both adapters 26 and 28 but without them rotating relative to each other.

As seen in FIG. 2, bore 46 of luer adapter 26 has a frustoconical bore portion 76 having walls which taper proximally and radially outwardly and which connect with a generally cylindrical bore portion 78 at the proximal end of the luer adapter. In the unlocked condition of device 12 (FIG. 2), the slotted collet 48 is received in bore portion 78 adjacent the tapered portion 76, and the distal end of grommet 30, including the enlarged head 64, is disposed in the tapered bore portion 76 in engagement with the tapered bore portion and the catheter 14.

With this construction, when it is desired to lock or hold catheter 14 against axial or longitudinal movement relative to luer adapter 26 and catheter locking adapter 28, relative rotation of the adapters 26 and 28 is effected in one sense of rotation. For example, if cap 23 and the sleeve adapter 22 are removed from the adapters 26 and 28, relative rotation of adapters 26 and 28, for example, clockwise rotation of locking adapter 28 when viewed from the right end in FIG. 2, while holding the luer adapter 26 stationary, causes the adapter 28 to advance distally or move distally axially relative to luer adapter 26 because of the threaded engagement between threads 44 and 52 on the adapters 26 and 28, respectively. This relative movement causes the distal end portion of slotted collet 48 and the head 64 of grommet 30 to move distally in the tapered bore portion 76 toward its narrow end to deform and compress distal portions of the grommet 30 into tighter frictional engagement with the catheter 14 and tapered bore portion 76. After predetermined relative rotation of the adapters 26 and 28 in this manner, the catheter 14 is locked or in fixed relation to the adapters 26 and 28, the condition shown for illustration in FIG. 6. In the locked condition of device 12, the inner side of flange 66 is flattened against catheter 14 and an increased and considerable portion of grommet 30 is in frictional contact with the outer surface of catheter 14. The distal end portions of collet 48 are urged inwardly to further compress portions of the collet against the catheter.

In both the catheter unlocked condition of device 10 (FIG. 2) and in the catheter locked condition of the device (FIG. 6), the grommet 30 completely surrounds and provides a fluid tight seal between the tapered portion 76 of the bore 46 of adapter 26 and the catheter 14 to prevent any fluid from flowing past the grommet. For example, no liquid or air can enter the right end of bore 56 and flow distally past the grommet 30. Also, air in the threaded portion of collar 50 cannot flow distally beyond the grommet head 64 because of its fluid tight engagement with the bore 46 and catheter 14.

In using the catheter placement device 10, an introducer needle and cannula assembly, indicated at 80 in FIG. 7, is employed to introduce the catheter 14 into the patient, for example, into a vein indicated at 82. The assembly 80 has a conventional hollow needle 84 passing through an introducer cannula 86 with the distal tip of the needle extending slightly beyond the distal tip of the cannula. Needle 84 has a needle hub or handle 87 which is preferably transparent and which is closed at the proximal end by a conventional filter 88. Filter 88 allows air, but not blood, to escape as blood flows into the needle and into the handle portion 87 during introduction of the cannula 86 into a vein to thereby indicate a successful venipuncture. After the distal ends of the needle 84 and cannula 86 are introduced into the vein 82 through the skin, the needle is disconnected from the cannula 86 while the cannula remains within the vein, the condition illustrated in FIG. 8.

The introducer cannula 86 may be a conventional catheter having a hub 90 with a female luer tapered bore portion 91 and luer lock ears 92 for connecting the cannula hub with the male luer lock connector 32 (FIGS. 2 and 3) of luer adapter 26. The cannula 86 may be made of Teflon, polypropylene, or other suitable plastic.

FIG. 8 also illustrates a step in connecting the catheter placement device 10 to the introducer cannula 86 while it is in the vein 82. In making this connection, the luer lock ears 92 are threadedly received in the threads 38 (FIGS. 2 and 3) of luer adapter 26 with the luer tapered bore 91 of the cannula hub 90 sealingly and frictionally receiving the male luer slip connector 34 of adapter 26. By inserting the cannula hub 90 into the luer connector 32 and rotating the sleeve connector 22 with adapter 26 in it, and in the clockwise direction indicated by the arrow in FIG. 8, a fluid tight connection is made between the distal end portion of bore 46 (FIG. 2) and the lumen of cannula 86. This rotation of sleeve connector 22 effects rotation of both adapters 26 and 28 with the adapters being maintained in fixed relative relation due to the splined connection of these members.

After the introducer cannula 86 is connected in fluid tight connection with luer adapter 26 of device 10, as indicated in FIG. 9, the catheter 14, within the protective sleeve 16, may be moved into the cannula 86 and then into the vein 82. This can be accomplished by holding the sleeve connector 22, such as by the fingers shown in phantom, and pinching the tubular sleeve 16 and catheter 14 at a position spaced from but somewhat close to the sleeve connector 22, and then moving both the catheter 14 and the sleeve 16 distally an incremental amount or selected distance to thereby move the catheter an incremental distance into the cannula 86. During this distal movement, a distal end portion of sleeve 16 axially collapses or folds upon itself in a generally irregular accordion-like fashion adjacent the sleeve connector 22. The catheter 14 and sleeve 16 are released and the fingers of the operator are again used to pinch the sleeve and catheter such as at a location on the sleeve that is straight or not collapsed, and to again move both the sleeve and the catheter 14 distally another incremental amount. These steps may be repeated until the catheter 14 has been positioned in a predetermined or desired location within the vein 82. In FIG. 9 the catheter is shown in a final or desired location with the distal portion of sleeve 16 adjacent the adapter 22 partially collapsed in accordion-like fashion as indicated at 93. This collapsed portion of the sleeve generally tends to at least partially straighten after complete insertion of the catheter.

Next, the hub 90 of introducer 86 may be grasped between the fingers of one hand, the sleeve connector 22 is grasped by the fingers of the other hand, and the connector 22 slid proximally off of both luer adapter 26 and catheter locking adapter 28, as indicated in FIG. 10. While holding the collar 36 of luer adapter 26 stationary, collar 50 of catheter locking adapter 28 may be rotated clockwise or in the direction of the arrow shown in FIG. 10 to effect axial movement of the adapters 26 and 28 toward each other to effect catheter locking, such as illustrated in FIG. 6. This step secures the catheter 14 against further axial movement relative to adapters 26 and 28. The introducer cannula and the adapters may be readily taped to the patient to thereby secure the catheter 14 in fixed relation to the patient. The catheter 14 may also be directly taped to the patient where desired. Because a relatively large area of the grommet is engaged with catheter 14 in the locked condition of the catheter, a substantial increase in torque is required to further turn the adapters 26 and 28 relative to each other and this provides an indication that the catheter is suitably locked in place.

The stylet 25, where used, may be removed by sliding it proximally out of the catheter 14, either before or after the catheter 14 has been locked in place relative to adapters 26 and 28. The stylet is shown in FIG. 10 having a wire 94, such as a metal or plastic wire, extending in the lumen of catheter 14 but it does not, of course, extend to or beyond the distal end of the catheter 14.

Catheter 14 is shown for illustration in FIG. 11 connected to a conventional source of infusion liquid, such as a saline solution indicated generally at 96. The source 96 is connected by a tube 97 having a conventional male luer lock connector 98 attached to it and which is connected to female luer lock hub 24 of catheter 14. By rotating the connector 98 such as in the direction of the arrow, while holding hub 24 stationary, the catheter 14 will be placed in sealed fluid communication with the source 96. Infusion liquid flows from source 96 and through catheter 14 to vein 82. Catheter 14, of course, may be connected to other devices or sources other than the infusion source 96.

The catheter locking device 12 can be returned to its unlocked condition (FIG. 2) from its locked condition (FIG. 6) by effecting relative rotation between the threaded coupling adapters 26 and 28 in the opposite sense from that described in connection with the locking of the catheter. For example, by holding the luer adapter 26 stationary and rotating catheter locking adapter 28 in the direction opposite to the arrow in FIG. 10, that is, in the counterclockwise direction as viewed from the right end of the device, the adapter 28 and grommet 30 move proximally relative to tapered bore portion 76 of adapter 26 tending to return the device 10 to its catheter unlocked condition of FIG. 2. This allows catheter 14 to again be manually moved longitudinally through the adapters 26 and 28, and grommet 30, so as to remove the catheter or reposition the catheter in the vein. The catheter locking assembly 12 can be repeatedly and readily locked and unlocked so as to lock and unlock the catheter relative to the adapters.

Where desired, the introducer cannula 86 may be removed from the patient while remaining on the catheter 14 so that only the catheter 14 extends into the patient. In such case, the adapters 26 and 28 can be taped to the patient after the introducer cannula is removed from the vessel.

Because sleeve adapter 22 is splined with adapters 26 and 28 respectively, it can be moved proximally away from the adapter 26 to be disengaged from it and then, while still surrounding and in splined connection with adapter 28, can be rotated to effect relative rotation between the adapters 26 and 28. Thus, the sleeve adapter 22 can be conveniently used to rotate the locking adapter 28 relative to the adapter 26 so as to lock or unlock catheter 14 if desired.

Feeding the pliable catheter 14 into a desired location in the blood vessel is easily and quickly accomplished with catheter placement device 10. This is because the resistance to movement of catheter 14 through grommet 30 in the distal direction is relatively low for easy distal movement into the blood vessel while the resistance to proximal movement is relatively high to prevent the catheter from returning or partially returning proximally from the patient when the catheter 14 and sleeve 16 are released after an incremental distal movement of the catheter. Even though the partially collapsed or gathered sleeve 16, such as indicated at 93 in FIG. 9, tends to straighten after release due to the resiliency of the sleeve and, in some cases, tends to move the catheter proximally, the relatively high resistance to proximal movement prevents or retards such proximal movement of the catheter. Also, if the catheter 14 is moved into a curved portion of a blood vessel, any return or proximal movement of the catheter is prevented or retarded by the relatively high resistance to its proximal movement. In this way, the catheter 14 tends to stay in the position in which it is moved during each incremental movement of catheter 14 into the introducer 86 and blood vessel 82. This avoids the necessity of additional incremental insertions and time to complete the catheter placement procedure and allows accurate catheter placement in a quick and easy manner.

With catheter placement device 10, the placement of the catheter 14 in a desired location in the blood vessel, as well as the locking of the catheter relative to the adapters 26 and 28, are readily accomplished so as to simplify the entire placement procedure. The catheter locking feature allows the introducer cannula, where used, and/or the adapters to be taped to the patient to thereby fix the catheter relative to the patient.

Figure 12:
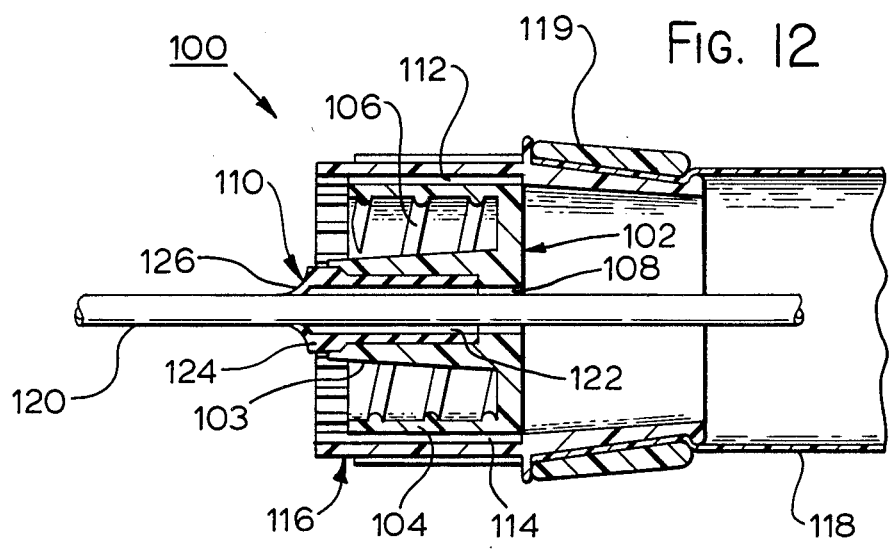
FIG. 12 is an enlarged fragmentary view in cross-section illustrating a second embodiment of the present invention.

A catheter placement device, indicated generally at 100, and which is a modified embodiment, is illustrated in FIG. 12 as including a male luer lock adapter 102 shown having a male luer tapered slip connector 103 surrounded by an integral luer lock collar 104 having internal threads 106. Adapter 102 is connectable to a complementary female luer lock connector such as that shown on hub 90 of introducer cannula 86. The adapter 102 has an opening or bore 108 extending through it. A resiliently compressible, elastomeric grommet 110, which may be similar or, as shown, identical to grommet 30, is inserted into the distal end portion of bore 108 in tight fitting relation with the adapter. The outer wall of adapter 102 has outer axial splines 112 which cooperate with internal splines 114 on a sleeve connector or adapter 116. Adapter 116 surrounds and is slidable relative to adapter 102, and can be removed from the adapter 102 if desired. The adapter 116 can be used to rotate adapter 102 into fluid tight engagement with the hub of an introducer cannula. A collapsible, flexible protective sleeve 118, for example, of polyethylene, is connected to sleeve adapter 116, such as by a lock ring 119 which is forced to slide over the distal end of sleeve 118 and the proximal end of sleeve adapter 116 to tightly clamp the distal end of sleeve 118 to adapter 116. In some cases, the distal end of sleeve 118 can be bonded or adhesively connected directly to adapter 116 without employing a lock ring. A flexible catheter 120 extends from within sleeve 118 through bore 108 of the adapter 100, and a bore, indicated at 122, of grommet 110.

In the construction of FIG. 12, the flexible catheter 120 cannot be locked to the luer adapter 102. However, the grommet 110 provides a relatively low resistance to movement of catheter 120 in the leftward or distal direction while providing a relatively high resistance to movement of the catheter 120 in the rightward or proximal direction in a manner similar to the manner in which the grommet 30 provides the relatively higher resistance to proximal movement of catheter 14 than to distal movement of it. As with grommet 30, grommet 110 has an enlarged head, indicated at 124, with a radially inwardly extending annular flange 126 at the distal end of the grommet. The flange 126 has an opening smaller than the outer diameter of catheter 120 so that the flange will be compressed or wedged between the walls of the grommet bore 122 and the outer surface of catheter 120 by rightward or proximal movement of catheter 120 to produce a substantial resistance to such movement tending to prevent inadvertent or undesired return movement of the catheter after each incremental insertion. The grommet flange 124 provides substantially less resistance to distal movement of the catheter 120 since the flange can readily bend distally away from the grommet, the condition shown in FIG. 12, without any wedging of the grommet between parts. Also, no fluid can flow into bore 108 past the grommet flange 126 and into the patient when the device is in use.

Catheter placement device 100 is used in a manner similar to that of device 10, except that with device 100 the catheter, such as at 120, cannot be locked relative to an adapter such as adapter 102. After an introducer cannula has been inserted into a blood vessel and the needle removed, the sleeve adapter 118 is rotated to rotate adapter 102 into fluid tight engagement with the luer lock connector of the introducer cannula. The pliable catheter 120 is then fed into the cannula and blood vessel of the patient in incremental steps until it is positioned in a desired location. The catheter and adapters may then be taped to the patient.

The embodiment shown in FIG. 12 may be advantageously used whenever catheter locking is not required or desired. Because of the relatively low resistance to distal catheter movement and relatively greater resistance to proximal movement, the catheter 120 is readily incrementally inserted into a desired location in the patient.

While the size of catheter used in the placement devices 10 and 100 can vary, small catheters of 14, 16 and 18 gauges having outer diameters of about 2.1, 1.7 and 1.4 milimeters, respectively, may be used.

As various changes could be made in the above constructions without departing from the scope of the invention, it is intended that all matter contained in the above description or shown in the accompanying drawings shall be interpreted as illustrative and not in a limiting sense.

I claim:

1. A catheter placement device comprising a first adapter having a bore therethrough, a luer connector at the distal end thereof connectable with a luer connector of an introducer cannula insertable into a vessel of a patient, a second adapter having a bore therethrough, an elastomeric grommet having a bore therethrough, a flexible catheter extending through said grommet bore and said adapter bores for insertion into an introducer cannula and vessel of a patient, the bore of one of said adapters being tapered with radially inwardly tapering sidewalls, said grommet being disposed in the bore of the other of said adpaters and extending into the bore of said one adpater, means for threadedly coupling said adapters to each ther, said grommet being movable toward the narrower end of said tapered bore and into increased frictional engagement with said catheter to thereby lock said catheter against axial movement relative to said adapters in response to predetermined relative rotation of said adapters, a flexible protective sleeve surrounding said catheter and being longitudinally collapsible to permit distal movement of said catheter through said grommet and adapter bores when a portion of said sleeve is manually pinched about said catheter and said sleeve portion and said catheter are moved distally relative to said adapters, and a cylindrical connector connected to the distal end of said sleeve and having a splined inner surface, said adapters having splined outer surfaces receivable in said connector with the splined surfaces of said adapters disposed in splined connection with the splined inner surface of said connector, said connector being slidable from each of said adapters.

2. The device of claim 1 further including detent means on one of said adapters, and radial flange means on the other of said adapters cooperating with said detent means to prevent inadvertent separation of said adapters when rotated relative to each other.

3. The device of claim 1 wherein said grommet includes passage restriction means frictionally engageable with said catheter for effecting a relatively low resistance to movement of said catheter through said grommet in a distal direction and relatively greater resistance to movement of said catheter therethrough in the proximal direction.

4. The device of claim 1 wherein said restriction means includes a radially inwardly extending flange at the distal end of said grommet frictionally engaging said catheter, said grommet flange being bendable into said grommet bore in tight frictional engagement between said grommet bore and said catheter in response to movement of said catheter in the proximal direction to effect a relatively high resistance to such catheter movement, said grommet flange being movable distally away from said grommet bore in response to distal movement of said catheter whereby resistance to such distal catheter movement is substantially less than the resistance to proximal movement thereof.

5. The device of claim 1 wherein said luer connector includes a luer slip member and an integral collar surrounding said luer slip member and having threads on the inner walls of said collar for threaded coupling engagement with luer lock means on an introducer cannula.

6. The device of claim 1 further including an end cap removably connected to said adapters enclosing the distal ends of said first adapter and said catheter.

7. A catheter placement device comprising a catheter locking assembly including a luer adapter having a bore therethrough, a male luer lock connector at the distal end adapted for connection with a female luer lock connector of an introducer catheter, an extension member connected with and extending proximally from said male luer lock connector, and threads on said extension member adjacent the distal end therof, said bore having a generally frusto-conical bore portion with its larger end proximal of its narrower end, a catheter locking adapter having a bore therethrough in registration with said leur adapter bore and including a flexible collet extending distally therefrom, a collar connected in spaced surrounding relation with said collet and having threads on the inner walls thereof for threaded connection with said luer adapter threads, and an elastomeric grommet in said collet including a generally cylindrical body having a bore, and an enlarged annular head at the distal end thereof extending distally of the distal end of said collet and engaged with said bore portion, said head including an annular radially inwardly extending flange at the distal end thereof having an opening in registration with said adapter and grommet bores, a pliable catheter extending through said grommet and said adapter bores and said flange opening and having a greater outer diameter than the diameter of said flange opening, said flange engaging said catheter and being movable generally distally of said grommet bore in response to distal movement of said catheter to effect a relatively slight resistance to distal movement of said catheter through said grommet bore, said flange being movable into said grommet bore in compressed relation between the walls of said grommet bore and said catheter to effect a substantially greater resistance to proximal movement of said catheter through said grommet bore than to distal movement thereof, said collet and grommet head being movable in said bore portion toward the narrower end thereof to compress said collet about said grommet and resiliently compress said grommot against said catheter and said bore portion to lock said catheter against axial movement relative to said adapters in response to relative rotation of said adapters in one rotational sense, said grommet effecting seal between said bore portion and around said catheter when said catheter is locked, said adapters being relatively rotatable in the opposite sense of rotation to unlock said catheter to permit axial movement thereof relative to said adapters, a collapsible sleeve covering a main portion of said catheter and permitting said catheter to be manually fed through said adapters without manually touching said catheter, and means for connecting said sleeve to said locking adapter, said means for connecting said sleeve to said locking adapter including a sleeve member slidable over said adapters, said sleeve member having splines on the inner surface thereof, said adapters having splines on the outer surfaces thereof cooperable with said sleeve member splines whereby rotation of said sleeve member effects rotation of each of said adapters when in said sleeve member, said sleeve member being removable from said adapters.

8. The device of claim 7 wherein said collet has longitudinally extending slots.

9. A catheter placement device comprising a pair of threadedly coupled relatively rotatable members each having a bore therethrough, and resiliently compressible grommet means having a bore therethrough disposed in the bore of one of said members for engagement with the other of said members, on elongate catheter axially movable selectively in proximal and distal direction through all of said bores, said members being axially movable toward each other and shaped to urge a portion of said grommet means into increased frictional engagement with said catheter to lock said catheter against axial movement relative to said members in response to predetermined relative rotation of said members, a flexible protective sleeve surrounding said catheter and being longitudinally collapsible to permit distal movement of said catheter through said grommet means bore and bores of said members when a portion of said sleeve is manually pinched about said catheter and said sleeve portion and said catheter are moved distally relative to said members, and a sleeve connector connected to said sleeve at the distal end thereof, said connector being slidable over at least one of said members and having abutment means on the radially inner side thereof, at least said last named member having abutment means on the radially outer side thereof cooperable with said abutment means on said connector so that rotation of said connector when extending over said last named member effect rotation thereof.

10. The device of claim 9 wherein both of said membres have abutment means cooperable with said abutment means on said connector and said connector is slidable over both of said members so that rotation of said connector when extending over both of said members effects rotation of both of said members.

11. The device of claim 10 wherein said abutment means on said connector and said members are complementary splines.

12. The device of claim 9 wherein one of said members includes a luer connector for connecting a cannula to the bores of said members.

13. The device of claim 9 wherein said grommet means has restriction frictionally engageable with said catheter to effect a substantially greater resistance to movement of said catheter through said grommet in the proximal direction than to movement thereof in the distal direction.

14. A catheter placement device comprising a pair of threadedly coupled relatively rotatable members each having a bore therethrough, a resiliently compressible grommet having a bore therethrough and including on elongate tubular portion extending into the bore of one of said members for engagement with the bore of the other of said members, a flexible catheter extending through all of said bores, said grommet bore being of greater diameter than the outer diameter of said catheter to allow said catheter to move therethrough with relatively low resistance, said members being axially movable to urge said grommet against said bore of said other member and into tight frictional engagement with said catheter to lock said catheter against movement relative to said members in response to predetermined relative rotation of said members, a flexible protective sleeve surrounding said catheter and being longitudinally collapsible to permit distal movement of said catheter through said grommet bore and bores of said members when a portion of said sleeve is manually pinched about said catheter and said sleeve portion and said catheter are moved distally relative to said members, and a sleeve connector connected to said sleeve at the distal end thereof, said connector being slidable over said members and having abutment means on the radially inner side thereof, said members have abutment means on the radailly outer sides thereof complementary with said abutment means on said connector so that rotation of said connector when extending over both of said members effects rotation of both said members.

15. The device of claim 14 wherein one of said members includes a luer connector for connecting an introducer cannula to the bore of said one member.

16. The device of claim 14 wherein said abutment means on said connector and said members are complementary splines.

17. A catheter placement device comprising a male luer lock adapter for connection with a female luer lock connector including a male slip connector having a bore, and a luer tapered outer surface, a collar connected to and surrounding said slip connector, thread means on the inner side of said collar, and an elongate elastomeric grommet having a bore therethrough, a tubular portion extending in the bore of said slip connector in frictional engagement therewith, and a head portion integral with said tubular portion and extending distally beyond the distal end of said slip connector, said head having a greater outer diameter and a greater wall thickness than that of said tubular portion, a pliable catheter movable in said bores, said head including an annular radially inwardly extending flange having an opening with a diameter smaller than the outer diameter of said catheter for frictional engagement with said catheter, said walls of said flange being of a thickness to move into said tubular portion with increased frictional forces applied by said flange to said catheter in response to proximal movement of said catheter relative to said flange, abutments on the radially outer side of said collar, a sleeve connector having abutments on the inner side thereof complementary to said abutments on the radially outer side of said collar for effecting rotation of said luer lock adapter upon rotation of said sleeve connector, and flexible sleeve adapted to surround at least a portion of said catheter connected to said sleeve connector.

18. A catheter placement device comprising a male luer adapter for connection with a female luer connector including a male slip connector having a luer tapered outer surface and a bore therethrough, and a collar connected to and surrounding said slip connector, a pliable catheter longitudinally movable in said bore, abutment means on the radially outer side of said collar, a sleeve connector longitudinally slidable over said collar and having abutment means on the inner side thereof complementary to and engageable with said abutment means on the radially outer side of said collar for effecting rotation of said luer adapter upon rotation of said sleeve connector, said complementary abutment means allowing said connector to slide longitudinally away from and off of said luer adapter, and a longitudinally collapsible protective flexible sleeve surrounding said catheter and fixedly connected to said sleeve connector to allow a portion of said sleeve to be manually grasped to move said catheter and a portion of said sleeve distally relative to said luer adapter to advance said catheter distally relative to said luer adapter.

19. The device of claim 18 including a grommet extending in said slip connector bore and having a bore therethrough, said catheter being movable in said grommet bore in frictional engagement with a portion of said grommet.

20. The device of claim 19 wherein said portion of said grommet includes a radailly inwardly extending flange at the distal end of said grommet movable distally in response to longitudinal distal movement of said catheter and movable proximally into increased frictional contact engagement with said catheter in response to longitudinal proximal movement of said catheter so that there is greater resistance to proximal movement than to distal movement of said catheter relative to said grommet.

21. The device of claim 18 wherein said abutment means on said sleeve connector and the outer side of said collar include longitudinal extending complementary splines.

* * * * *